(12) United States Patent
Salanitro

(10) Patent No.: US 6,365,397 B1
(45) Date of Patent: *Apr. 2, 2002

(54) BACTERIAL CULTURE WHICH DEGRADES METHYL-TERT-BUTYL ETHER TO CARBON DIOXIDE

(75) Inventor: Joseph Patrick Salanitro, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/439,905

(22) Filed: Nov. 12, 1999

(51) Int. Cl.⁷ .............. B09B 3/00; C12N 1/12; C12N 1/20
(52) U.S. Cl. .............. 435/262.5; 435/252.1; 435/821; 435/822; 210/600; 210/601
(58) Field of Search .............. 435/252.1, 821, 435/822, 262.5; 210/600, 601

(56) References Cited

U.S. PATENT DOCUMENTS

| | | | |
|---|---|---|---|
| 4,009,099 A | 2/1977 | Jeris | 210/612 |
| 4,391,887 A | 7/1983 | Baumgarten et al. | 435/42 |
| 4,415,454 A | 11/1983 | Fuchs | 210/616 |
| 5,474,934 A | 12/1995 | Adamus et al. | 435/262.5 |
| 5,536,410 A | 7/1996 | Kitatsuji et al. | 210/626 |
| 5,750,364 A | 5/1998 | Salanitro | 435/42 |
| 5,811,010 A | 9/1998 | Salanitro | 210/610 |
| 5,814,514 A * | 9/1998 | Steffan et al. | 435/262 |
| 5,902,734 A | 5/1999 | Salanitro | 435/42 |
| 6,040,154 A * | 3/2000 | Fayolle et al. | 435/42 |

OTHER PUBLICATIONS

K. Mo, et al., Appli. Microbiol BioTechnol. (1997) 47:69–72.

" Biodegradation of Methyl tert–Butyl Ether by a Bacterial Pure Culter", by Jessica Hanson et al; Applied and Environmental Microbiology, Nov. 1999, pp. 4788–4792.

" Characterization of MTBE–Degrading Bacterial Isolates and Associated Consortia", by Jessica Hanson and Kate Snow; presented at the MTBE Workshop on Jun. 16, 1998, pp. 1 of 1.

"Biodegradation of the Gasoline Oxygenates Methyl tert–Butyl Ether, Ethyl tert–Butyl Ether, and tert–Amyl Methyl Ether by Propane–Oxidizing Bacteria", Robert J. Steffan et al., Applied and Environmental Microbiology, Nov. 1997, p. 4216–4222.

* cited by examiner

Primary Examiner—David M. Naff
Assistant Examiner—Deborah K. Ware
(74) Attorney, Agent, or Firm—Y. Grace Tsang

(57) ABSTRACT

A biologically pure bacterial culture has been isolated by a dilution enrichment process from a mixed bacterial culture, obtained by the enrichment of an activated sludge taken from a biotreater for treating wastewater in a Chemical plant. The mixed bacterial culture is capable of degrading aerobically a branched alkyl ether or a branched alkyl alcohol, particularly a tertiary carbon atom-containing alkyl ether or alkyl alcohol, more particularly MTBE or t-butyl alcohol, to $CO_2$. The biologically pure bacterial culture is capable of cleaving the ether linkage of methyl t-butyl ether (MTBE) with the transient formation of t-butyl alcohol (TBA) which is subsequently degraded completely to $CO_2$.

18 Claims, 1 Drawing Sheet

BACTERIAL CULTURE WHICH DEGRADES METHYL-TERT-BUTYL ETHER TO CARBON DIOXIDE

FIELD OF THE INVENTION

This invention relates to a pure bacterial culture for degrading branched alkyl ethers, such as methyl t-butyl ether (MTBE), and branched alcohol such as t-butyl alcohol (TBA). The invention also relates to a process for preparing such culture.

BACKGROUND OF THE INVENTION

Alkyl-alkyl ethers (R—O—R) such as methyl t-butyl ether (hereinafter "MTBE") are being used as octane-enhancers in the reformulation of low volatility unleaded gasoline blends and for reducing the emission of volatile organic compounds from engines. In general, alkylethers, especially those alkylethers which have only one ether linkage and without other functional groups, are chemically stable compounds and there is little information on their biodegradability in soil, groundwater and activated sludge environments. The very slow rate of alkylether degradation by indigenous microbes in soils and biosludges may be attributed to the very stable and chemically unreactive ether linkage, the inability of these compounds to be transported into cells and/or the lack of inducible or existing enzyme activities (e.g. oxygenases, hydroxylases) which can attack the ether bond.

It is known that MTBE can persist in groundwater from accidental spills of unleaded gasoline from underground storage tanks. Certain mixed bacterial culture(s) have been used to degrade MTBE. But, it is desirable to use a pure bacterial culture for degrading MTBE and TBA to effectively biotreat groundwater, wastewater, tank bottom wastes or soils containing these tertiary-carbon-containing ether and alcohols. This is because relatively large quantities of mixed culture are typically needed for degrading or remediating MTBE or TBA. However, only minor portions of mixed cultures contain microbes which are able to degrade MTBE or its metabolites. It is more costly to mass produce mixed cultures than pure cultures to obtain the same quantity of MTBE degradation activities.

U.S. Pat. No. 5,750,364, assigned to Shell Oil Company having J. P. Salanitro as the inventor, describes a mixed bacterial culture capable of degrading MTBE and TBA.

K. Mo, et al. *Appl Microbiol Biotechnol* (1997) 47:69–72 proposes isolating from activated sludge and fruit of the Gingko Tree three pure cultures, classified as belonging to the genuses Methylobacterium, Rhodococcus, and Arthrobacter, which are capable of degrading MTBE. However, the data presented by Mo proposes that only a minor portion of the MTBE was degraded by the cultures and very little if any, of MTBE degraded to carbon dioxide within the time frame of the experiment.

Thus, there remains a need for a pure bacterial culture capable of degrading an alkyl ether, especially a branched alkyl ether, specifically a tertiary carbon atom-containing ether such as MTBE, to carbon dioxide effectively within a short period of time under aerobic condition. There is also a need for the same for degrading branched alcohols, especially tertiary carbon atom-containing alcohols, such as t-butyl alcohol (TBA). The culture would be useful for treating wastes and groundwater contaminated with ethers, especially branched alkyl ethers such as MTBE, and branched alcohols such as TBA.

SUMMARY OF THE INVENTION

This invention relates to (a) a pure bacterial culture capable of degrading alkylethers, especially branched alkylethers including MTBE and branched alcohols such as t-butyl alcohol, under aerobic conditions; (b) a process for preparing such pure bacterial culture; (c) a process for the aerobic degradation of ethers, especially branched alkylethers such as MTBE, using a pure bacterial culture prepared from activated sludges; (d) a process for remediating wastewater and groundwater containing ethers, especially branched alkylethers such as MTBE, to reduce the alkylether(s) content thereof by growing in the presence of said wastewater and groundwater a population of a pure bacterial culture prepared from activated sludges; and (e) the use of said pure culture for degrading or remediating t-butyl alcohol containing aqueous solutions or groundwater.

BRIEF DESCRIPTION OF THE DRAWINGS

The drawing (FIG. 1) illustrates a specific embodiment of the present invention in which the specific activity of the pure culture is increased (induced) by incubating with MTBE.

DETAILED DESCRIPTION OF THE INVENTION

Figure 1:
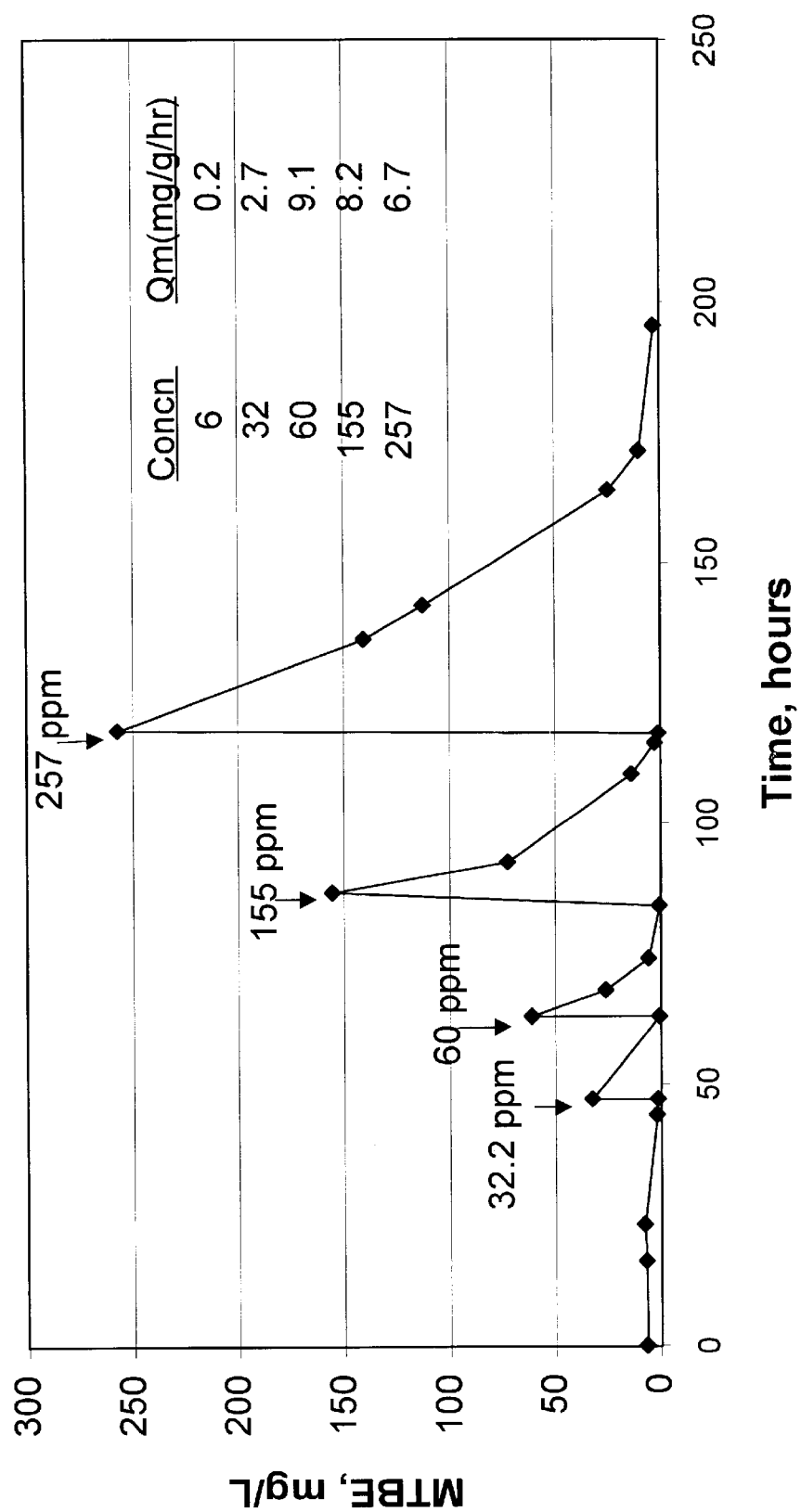

The present invention involves a pure bacterial culture capable of degrading aerobically a branched alkyl ether, particularly a tertiary carbon atom-containing alkyl ether, more particularly MTBE, to $CO_2$ The bacterial culture is capable of cleaving the ether linkage of methyl t-butyl ether (MTBE) with the transient formation of t-butyl alcohol (TBA) which is subsequently degraded completely to $CO_2$. As a particular embodiment of the present invention, The novel bacterial culture can also metabolize other linear and branched ethers. Non-limiting and illustrative examples of the linear and branched ethers include diethyl ether (DEE), dimethyl ether (DME), methyl ethyl ether (MEE), methyl n-propyl ether (MPE), ethyl n-propyl ether, methyl isopropyl ether, ethyl isopropyl ether, diisopropyl ether (DIPE), ethyl t-butyl ether (ETBE) or methyl-t-amyl ether. As a specific embodiment of the present invention, the present composition also includes any composition derived from the pure bacterial culture. Illustrative examples of the compositions derived from the bacterial culture include, but not limited to, member(s) of, fragment(s) of bacterial culture, membrane fragment(s) of bacterial culture, enzymes extracted and/or isolated from the bacterial culture, lyophilized and/or dried culture, lyophilized and/or dried fragments of culture, lyophilized and/or dried enzymes derived from said culture, bacterial culture and/or fragment(s) thereof and/or enzymes derived therefrom bound to a carrier and/or binder and/or fixed bed, etc. Any method known to one skilled in the art for making composition derived from the culture including but not limited to extraction or fragmentation to obtain active ingredients/fragments thereof is within the scope of the present invention. As one non-limiting example of the present invention, the culture can be first fragmented by sonification or lysing with lysozyme and/or a compound such as a chelating compound, followed by salting out the enzyme fractions using ammonium sulfate or NaCl.

As a specific embodiment of the present invention, the instant pure culture belongs to the family Actinomycetes. As another specific embodiment of the present invention, the pure culture isolated is a Rhodococcus species. As a particular embodiment of the present invention, the present culture is a pure culture strain having the ability to degrade MTBE; specifically the ability to degrade MTBE in 70 hours; more specifically the ability to degrade at least 10% of the MTBE present in a MTEE-containing mixture to carbon dioxide in 70 hours; even more specifically the ability to degrade both MTBE and TBA, preferably to carbon dioxide in 70 hours; more specifically the ability to degrade at least 10% of the MTBE and/or TBA added to the culture at a concentration of 0.01 to 500 ppm, to carbon dioxide within 70 hours; particularly the ability to degrade to carbon dioxide MTBE and one or more of the following ether compounds: diisopropyl ether, ethyl-t-butyl ether, di-t-butyl ether, diisobutyl ether, isopropyl isobutyl ether, isopropyl t-butyl ether, t-amylmethyl ether, t-amylethyl ether, t-amyl ethyl ether, t-amyl propyl ether, t-amylisopropyl ether, t-amyl-n-butyl ether, t-amyl isobutyl ether, and t-amyl methyl ether within 70 hours; more particularly the ability to degrade to carbon dioxide MTBE and one or more of the following tertiary carbon-containing ether compounds: ethyl-t-butyl ether, t-amyl-n-butyl ether, t-amylisobutyl ether, isopropyl t-butyl ether, t-amyl ethyl ether, t-amylpropyl ether, t-amylisopropyl ether, and methyl t-amyl ether within 70 hours.

The present invention also relates to a process for preparing a pure bacterial culture capable of degrading branched ether from a mixed bacterial culture capable of degrading the same. As a particular aspect of the present invention, it is provided with a process for isolating a pure culture from a mixed bacterial culture. Any method known to one skilled in the art which is able to isolate the MTBE-degrading pure culture from a mixed culture capable of degrading branched ether such as MTBE is within the scope of the present process. Non-limiting example of the process suitable for isolating the pure culture(s) of the present invention includes enhancing isolation of the pure microbe (s) capable of degrading MTBE by first making dilution enrichments of the present mixed culture(s). As an illustrative example, the dilution enrichments are made by adding sterile mineral dilution medium( such as Bushnell-Haas minerals (BH)-Difco-sterile) containing about 0.01–1000 mg/L, specifically about 0.1–100 mg/L, more specifically from about 1–10 mg/L MTBE to the mixed culture at about from 5:1 to 0.2:1, specifically from about 3:1 to about 0.3:1 ratio, more specifically at about 1.5:1 to 1:1.5 ratio. At certain time intervals such as weekly, biweekly or monthly, a portion of the culture volume was aseptically removed and replaced with fresh sterile dilution medium added to the remaining culture. The dilution enrichment method was continued for an extended period of time of about 2–60 weeks, specifically of about 4–25 weeks, and more specifically of about 7–14 weeks at about 10–40° C., specifically about 20–35° C. and more specifically at 23° C. to 32° C. until a dilute suspension of bacteria degrading MTBE consistently degraded MTBE before each transfer interval. This dilution enriched culture can subsequently be streaked onto sterile Petri plates containing minerals and solidifying agent such as 1.5% Difco Agar. Plates were incubated at about 10–40° C., specifically about 20–35° C. and more specifically at 23° C. to 32° C. and observed for the appearance of colonies after about 1–70 days, specifically after 2–50 day, more specifically after 3–5 days. All of the colonies were individually picked with sterile needles and inoculated containers/vials containing sterile mineral medium (such as BH medium) containing about 0.01–1000 mg/L, specifically about 0.1–100 mg/L, more specifically from about 1–10 mg/L MTBE. The cultures were incubated at about 10–40° C., specifically about 20–35° C. and more specifically at 23° C. to 32° C. and the loss of MTBE from the headspace of containers/vials was determined. Isolate(s) which degrade MTBE effectively preferably without the appearance of intermediates such as t-butyl alcohol are identified as pure culture capable of degrading MTBE and preferably also TBA effectively.

One of the mixed cultures suitable for preparing the present pure culture is a mixed culture having the identifiable characteristic of the mixed culture with ATCC No. 202057. As used herein, the term "identifiable characteristic of the mixed culture MC-100 with ATCC No. 202057" means the ability to degrade MTBE; specifically the ability to degrade MTBE in 70 hours; more specifically the ability to degrade at least 10% of the MTBE present in a MTBE-containing mixture to carbon dioxide in 70 hours; even more specifically the ability to degrade both MTBE and TBA, preferably to carbon dioxide in 70 hours; more specifically the ability to degrade at least 10% of the MTBE and/or TBA added to the culture at a concentration of 0.01 to 500 ppm, to carbon dioxide within 70 hours; particularly the ability to degrade to carbon dioxide MTBE and one or more of the following ether compounds: diisopropyl ether, ethyl-t-butyl ether, di-t-butyl ether, diisobutyl ether, isopropyl isobutyl ether, isopropyl t-butyl ether, t-amylmethyl ether, t-amylethyl ether, t-amyl ethyl ether, t-amyl propyl ether, t-amylisopropyl ether, t-amyl-n-butyl ether, t-amyl isobutyl ether, and t-amyl methyl ether within 70 hours; more particularly the ability to degrade to carbon dioxide MTBE and one or more of the following tertiary carbon-containing ether compounds: ethyl-t-butyl ether, t-amyl-n-butyl ether, t-amylisobutyl ether, isopropyl t-butyl ether, t-amyl ethyl ether, t-amylpropyl ether, t-amylisopropyl ether, and methyl t-amyl ether within 70 hours.

As a specific embodiment of the present invention, the mixed cultures suitable for preparing the present pure culture is available as product MC-100 from Shell Oil Company and its affiliate Equilon Enterprises LLC in Houston, Tex.

As one embodiment of the present invention, the isolated pure bacteria culture can be grown to obtain a larger population of a larger quantity of the culture by growing in a sugar (such as glucose) containing BH mineral solution. As another embodiment of the present invention, the isolated pure culture is grown in an MTBE-containing mineral media. Particularly, the culture is grown in a sugar containing mineral solution and the MTBE degrading activity is induced by adding MTBE to the culture. As a specific aspect of this embodiment, the MTBE degrading activity, i.e. the capability of degrading MTBE (the concentration of the MTBE degraded within about five hours, specifically about 10 hours, more specifically about 50 hours) is increased by at least 25%, preferably by at least 50%, more preferably by at least 100% after incubating with 1–1000 mg/L, specifically about 5–500 mg/L, more specifically about 20–200 mg/L for less than 10 hour, specifically for about less than 20 hours, and more specifically for less than 50 hours.

As still another aspect of the present invention, the specific activity of the present pure culture is from about 0.1 to about 100, preferably from about 1 to about 50, more preferably from about 5 to about 30 mg MTBE/g cells/hr at 9° C.

As a particular aspect of the present invention, the present pure bacterial culture is isolated from a mixed bacterial culture enriched from an activated sludge. The mixed culture is enriched by adding a branched alkyl ether such as MTBE to an activated sludge, specifically activated sludge obtained from a chemical plant, petrochemical plant or a refinery, more specifically from a biotreater located in a wastewater treatment plant in a refinery or a petrochemical plant. As a specific embodiment of the present invention, The mixed culture and the method for preparing thereof can be found in U.S. Pat. No. 5,750,364, assigned to Shell Oil Company having Joe P. Salanitro as the inventor. The entire description of U.S. Pat. No. 5,750,364 is herein incorporated by reference.

As a specific embodiment of the present invention, the activated sludge is retrieved from the biotreater located in a wastewater treatment plant of a chemical plant. As a still more specific embodiment of the present invention, the activated sludge is retrieved from the biotreater of the South Effluent Treater for treating wastewater from the Chemical Plant of Shell Deer Park Manufacturing Complex located at 5900 Highway 225, Deer Park Tex. 77536.

The present mixed culture is prepared by adding a branched alkyl ether to the biosludge (activated sludge) and incubating for a period of time. As one specific embodiment of the present invention, the biosludge is first added to a mineral nutrient solution. One specific, but non-limiting, example of the mineral solution is Sturm solution comprising $KH_2PO_4$, $K_2HPO_4$, $Na_2HPO_4.2H_2O$, $MgSO_4.7H_2O$, $NH_4Cl$ $(NH_4)_2$ $SO_4$, and $FeCl_3.6H_2O$. Incubation using other nutrient solution known to those skilled in the art is within the scope of the present invention. The concentration of the biosludge in the incubated medium (culture) can be any suitable amount which would produce sufficient concentration of ether degrading bacteria. In a specific embodiment of the present invention, from about 50 mg to about 5000 mg, more specifically from about 50 mg to about 1500 mg, still more specifically from about 300 to about 800 mg, of the biosludge solids are added to every liter of the incubation medium.

The above mixed culture is enriched by adding a suitable amount of branched alkyl ether. In a specific embodiment of the present invention, about 5–5000 mg, more specifically about 10–500 mg, still more specifically about 30–50 mg, of the branched alkyl ether is added to every liter of the culture (incubation medium or mixture).

The mixture or culture is incubated for a period of time. The typical temperature at which the culture is incubated ranges from about 5° C. to about 80° C., specifically from 10° C. to about 60° C., more specifically from about 15° C. to about 35° C., still more specifically from about 22° C. to about 25° C. Periodically, a sample of the culture (or supernatant) is withdrawn for branched alkyl ether analysis. A culture is active in degrading branched alkyl ether if there is detectable reduction of the concentration of the branched alkyl ether in the culture being enriched, after taken into account of the amount of branched alkyl ether evaporated. As an illustrative but non-limiting example, a culture which is considered very active in degrading branched alkyl ether will degrade a solution containing about 0.001–5000 ppm, more specifically about 0.01–500 ppm, still more specifically about 0.05–100 ppm, of branched alkyl ether, especially MTBE, by from about 10% to about 100%, specifically from about 30% to about 100%, more specifically from about 50% to about 100%, still more specifically from about 80% to about 100% to form a metabolic product of MTBE, such as TBA, t-butylformate, isopropanol and lactate in from about 2 hours to about 70 hours, specifically from about 2 hours to about 12 hours, more specifically from about 3 hours to about 5 hours. As an illustrative nonlimiting example, a culture of the present invention is capable of degrading a solution containing 120 mg/L of MTBE to close to less than 1 ppb of MTBE in about 4 hours or less.

In one specific embodiment of the present invention, the mixture of the activated sludge and the mineral solution is first flushed with oxygen before the addition of the branched alkyl ether.

In still another specific embodiment of the present invention, periodically, a portion in an amount of about 5–80%, specifically about 10–70%, more specifically about 40–60%, of the supernatant of the culture is withdrawn and fresh mineral or nutrient solution is added to at least partially replace the amount of supernatant withdrawn. The withdrawal can be conducted at an interval of about 1–30 days, specifically 2–10 day, more specifically about 5–8 days.

As another specific embodiment of the present invention, multiple additions of branched alkyl ether are subsequently made to the culture (incubating medium) after the first addition of the branched alkyl ether. The subsequent additions were made at least two days after the first addition of the branched alkyl ether. As a specific aspect of this embodiment, sufficient amount of branched alkyl ether is added either immediately after each withdrawal of the supernatant or simultaneously with the addition of the replacement portion of mineral or nutrient solution, thereby compensating the loss of the branched alkyl ether resulted from the withdrawal. As another specific aspect of this embodiment, sufficient alkyl ether is added each time designed to maintain the alkyl ether concentration at about 50–150%, specifically about 80–120%, of the original concentration. Preferably, multiple additions (re-inoculation) of the activated sludge is made to the culture periodically, such as at an interval of about 2–60 days, specifically about 3–30 days, more specifically about 5–10 days. In a specific aspect of this embodiment, from about 50 mg to about 5000 mg, more specifically from about 50 mg to about 1500 mg, still more specifically from about 300 to about 800 mg, of biosludge solids are added to every liter of the incubation medium at each re-inoculation. Illustrative examples of the branched alkyl ether suitable for the enrichment of the mixed culture suitable for preparing the pure culture of the present invention include, but not limited to, MTBE, diisopropyl ether, ethyl t-butyl ether, di-t-butyl ether, diisobutyl ether, isopropyl isobutyl ether, isopropyl t-butyl ether, isopropyl isobutyl ether, t-amyl methyl ether, t-amyl ethyl ether, t-amyl propyl ether, t-amyl isopropyl ether, t-amyl n-butyl ether, t-amyl isobutyl ether, t-amyl methyl ether, ethyl ether etc. As a preferred embodiment of the present invention, methyl t-butyl ether (MTBE) is used in the enrichment of the bacterial culture to produce a MTBE degrading mixed culture. The enrichment process typically lasts from about 1 month to about one year, more typically from about 1.5 months to 5 months, more typically from about 2 months to about 4 months. As a specific embodiment of the present invention, the mixed culture useful for isolating the present pure culture is a culture with ATCC No. 202057.

The present invention further involves a process for degrading ethers, including alkylethers and aromatic ethers utilizing the above-mentioned novel pure culture by mixing or growing the aforementioned culture or composition derived therefrom with the ether (or a solution containing the ether) to be degraded. The alkylethers include branched alkyl ether and linear alkyl ethers. Specifically, the process of the present invention is effective in degrading branched alkyl ether, particularly MTBE. As a specific embodiment of the present invention, the ether to be degraded can be an ingredient in an aqueous solution such as groundwater and wastewater, a solid mixture such as soil, etc. The degradation is preferably conducted under an oxygen-containing atmosphere, such as aerobic conditions. The degradation can be conducted at a temperature from about 5° C. to about 80° C., specifically from about 10° C. to about 60° C., more specifically from about 15° C. to about 35° C., still more specifically at ambient temperature.

As a specific embodiment of the present process, the pure bacterial culture is used to remediate groundwater and wastewater containing ether, specifically alkyl ether, more specifically MTBE.

It is known that when MTEE-containing fuels are accidentally released to the subsurface, this alkyl ether is the most water soluble and persistent compound in ground water. Other branched alkyl ethers which behave similarly and have also been considered by the oil industry as octane enhancers for motor fuels are diisopropyl ether (DIPE), ethyl tertiary butyl ether (ETBE) and methyl tertiary amyl ether (MTAE). The present invention thus provides an effective biological process for remediating these ethers accidentally released to the subsurface such as groundwater, wastewater and soil. In a specific embodiment of the present invention, the ethers can be completely mineralized to carbon dioxide by a suitable culture prepared by the aforementioned enrichment process. Hence, the remediation process can be substantially free of environmentally undesirable end products.

The present culture is capable of degrading/remediating ether(s), specifically branched alkyl ether(s), more specifically MTBE, in an aqueous mixture containing from about 0.001 ppm to about 5000 ppm, specifically from about 0.01 ppm to about 500 ppm, more specifically from about 0.05 ppm to about 100 ppm of the ether(s); to reduce the content thereof by from about 10% to about 100%, specifically from about 30% to about 100%, more specifically from about 50% to about 100%, still more specifically from about 80% to about 100% in from about 2 hours to about 70 hours, specifically from about 2 hours to about 12 hours, more specifically from about 3 hours to about 5 hours, by growing in the aqueous mixture the culture of the present invention.

As a specific embodiment of the present invention, the concentration of the present pure culture used for degrading or remediating branched ether or MTBE is from about 50 to about 10,000, specifically from about 100 to about 3,000, and more specifically from about 1,000 to about 2500 mg of dry weight of cells per liter or Kg mixture, wastewater, groundwater or soil comprising from about 3 ppb to about 1000 ppm, specifically from about 5 ppb to about 500 ppm, more specifically from about 10 ppb to about 200 ppm of MTBE; said pure culture is capable of degrading the MTBE to carbon dioxide and water by about 10 to 100 percent, preferably by about 50 to 100 percent, more preferably by about 80 to 100 percent, still more preferably by about 90 to 100 percent, still more preferably by about 95 to about 100 percent in less than about 70 hours, preferably in less than about 50 hours, more preferably in less than about 30 hours. As a preferred embodiment, the pure culture is capable of degrading MTBE present at the above-mentioned concentration down to about less than 100 ppb, specifically less than 40 ppb, more specifically less than 5 ppb, more specifically less than 1 ppb, in less than 70 hours, preferably in less about 50 hours, more preferably in less than 30 hours, still more preferably in less than 15 hours at a temperature of about 5 to about 35° C.

The present invention further relates to a composition suitable for degrading MTBE and/or TBA comprising the present pure bacterial culture and the present mixed bacterial culture.

The present invention further relates to a process for aerobically degrading a branched alkyl ether, specifically a tertiary carbon-containing alkyl ether, in a branched alkyl ether-containing mixture, preferably to carbon dioxide utilizing the present pure culture. The mixture can be, but not limited to, an aqueous medium, a soil medium, or a mixture of soil and water, such as waste water, ground water, soil, etc. As a specific embodiment, the present process relates to aerobically degrading MTBE in a MTBE-containing mixture, which process comprises growing in the presence of MTBE-containing mixture the present pure culture, or its derivatives to reduce the concentration of the MTBE in the mixture. As one specific embodiment, the branched alkyl ether-containing mixture comprises from about 0.001 ppm to about 5000 ppm, specifically from about 0.01 ppm to about 500 ppm, more specifically from about 0.05 ppm to about 100 ppm of the ether(s); and the present process reduces the content of branched alkyl ether, specifically MTBE, by from about 10% to about 100%, specifically from about 30% to about 100%, more specifically from about 50% to about 100%, still more specifically from about 80% to about 100% in from about 2 hours to about 70 hours, specifically from about 2 hours to about 12 hours, more specifically from about 3 hours to about 5 hours. As a specific aspect of the present invention, the process degrades the branched alkyl ether, specifically MTBE, to carbon dioxide and water. The present invention further relates to a process for treating groundwater or wastewater containing a branched alkyl ether such as diisopropyl ether, ethyl-t-butyl ether, di-t-butyl ether, diisobutyle ether, isopropyl isobutyle ether, isopropyl t-butyl ether, t-amylmethyl ether, t-amylethy ether, t-amyl ethyl ether, t-amyl propyl ether, t-amylisopropyl ether, t-amyl-n-butyl ether, t-amyl isobutyl ether, and t-amyl methyl ether, especially a tertiary carbon-containing ether using the present pure culture or a mixture of the present pure culture with the present mixed culture.

The present invention further relates to a process for degrading or remediating branched alkyl alcohol, specifically a tertiary-carbon atom-containing alcohol, more specifically t-butyl alcohol, in a branched alkyl alcohol-containing mixture such as groundwater and waste water. The alcohol is degraded to carbon dioxide and water. As a specific embodiment, the present process relates to aerobically degrading t-butyl alcohol in a t-butyl alcohol-containing mixture, which process comprises growing in the presence of t-butyl alcohol-containing mixture the present culture, or its derivatives including the present pure culture to reduce the concentration of the t-butyl alcohol in the mixture to a lower concentration. As one specific embodiment, the aqueous branched alkyl ether-containing mixture comprises from about 0.001 ppm to about 5000 ppm, specifically from about 0.01 ppm to about 500 ppm, more specifically from about 0.05 ppm to about 100 ppm of the ether(s); and the present process reduces the content of t-butyl alcohol, by from about 10% to about 100%, specifically from about 30% to about 100%, more specifically from about 50% to about 100%, still more specifically from about 80% to about 100% in from about 2 hours to about 70 hours, specifically from about 2 hours to about 12 hours, more specifically from about 3 hours to about 5 hours.

The present process further relates to simultaneously degrading both MTBE and TBA in an aqueous or soil medium containing both MTBE and TBA using the present pure bacterial culture or mixture of pure culture with present mixed culture.

The invention will be illustrated by the following illustrative embodiments which are provided for illustration purpose only and are not intended to limit the scope of the instant invention.

Illustrative Embodiments

The following illustrative embodiments describe typical techniques of the present invention.

Part A: Isolation of Pure Culture

Dilution enrichments of the present mixed culture were made to enhance isolation of a specific microbe degrading MTBE. In this method, a mixed culture MC-100 (ATCC No. 202057) enriched from activated sludge was used to isolate pure culture. The mixed bacterial culture MC-100 was prepared using the method described in U.S. Pat. No. 5,750,364. The MTBE and TBA degrading activity of MC-100 at 9° C. at 330 mg/L TSS is demonstrated in the following Table:

TABLE 1

DEGRADATION OF MTBE UTILIZING MIXED CULTURE MC-100

| Time (hr) | MTBE Conc (ppm) | | | | | |
|---|---|---|---|---|---|---|
| | 6.5 | 14 | 19.2 | 40 | 100 | 190 |
| 0 | 6.5 | 14 | 19.2 | 40 | 100 | 190 |
| 0.5 | 5.5 | 10.8 | 19.2 | 37 | 100 | 190 |
| 1 | 4 | 9.4 | 15.4 | 30 | 90 | 197 |
| 4 | 2.1 | 5 | 14.1 | | 90 | |
| 5 | 1.2 | 5.4 | 11.2 | 30 | 82 | 176 |
| 7 | 0.7 | 3.5 | 4.4 | 19 | 82 | 178 |
| 24 | 0 | 0.44 | 0.27 | 8.8 | 53.3 | 150 |
| 48 | | 0 | 0.08 | 0.11 | 26.4 | 140 |
| 72 | | | 0 | 0 | 23.9 | 145 |
| 96 | | | | | 10.8 | 140 |
| 168 | | | | | 0 | 140 |
| 192 | | | | | | 127 |

Experimental Conditions: MC-100 with 330 mg/L TSS @ 9° C.

TABLE 2

Degradation of TBA Utilizing Mixed Culture MC-100

| Time (hr) | TBA Conc (ppm) | | | | |
|---|---|---|---|---|---|
| | 1.1 | 2.6 | 5.6 | 14 | 28 |
| 0 | 1.1 | 2.6 | 5.6 | 14 | 28 |
| 0.5 | 1.2 | 2.7 | | | |
| 2 | 0.9 | 2.3 | 4.4 | 16 | 28 |
| 4 | 0.66 | 1.5 | | | |
| 6 | 0.47 | 1.4 | 4 | 11 | 26 |
| 24 | 0.094 | 0.26 | 1.1 | 5.9 | 17 |
| 48 | <0.01 | <0.01 | 0.024 | 0.27 | 10 |
| 72 | | | <0.01 | <0.01 | 3 |
| 144 | | | | | <0.1 |

The pure culture was prepared by adding ten ml of the MC-100 ml sterile Difco Bushnell-Haas (MgSO$_4$, 200 mg/L; CaCl$_2$, 20 mg/L; KH$_2$PO$_4$, 1000 mg/L; K$_2$HPO$_4$ 1000 mg/L; NH$_4$NO$_3$ 1000 mg/L; FeCl$_3$, 50 mg/L, pH 7.0) minerals medium (3.5 g/L; referred to as BH) in stoppered serum bottles containing 1–5 mg/L MTBE. At weekly intervals, half of the culture volume (10 ml) was aseptically removed and 10 ml fresh sterile BH medium added to the remaining 10 ml of culture. The dilution enrichment method was continued for at least 2–3 months at 25° C. until a dilute suspension of bacteria degrading MTBE consistently degraded MTBE before each transfer interval. This dilution enrichment culture was subsequently streaked onto sterile Petri plates containing BH minerals plus 1.5% Difco Agar as solidifying agent. Plates were incubated at 25° C. or 30° C. and observed for the appearance of colonies after 3–5 days. Approximately 20 colonies were picked with sterile needles and inoculated into 20 serum vials containing sterile BH medium and 1–10 mg/L MTBE. These cultures were incubated at 25–30° C. and the loss of MTBE from the headspace of serum vials was determined. One isolate (SC-100) completely degraded MTBE without any significant appearance of intermediates such as t-butyl alcohol.

Part B. Degradation of MTBE by Pure Culture

The pure culture isolate was grown in R$_2$A broth medium (yeast extract 0.5 g/L; peptone 0.5 g/L; casein acid hydrolyzate, 0.5 g/L; soluble starch, 0.5 g/L; glucose 0.5 g/L; KH$_2$PO$_4$, 0.3 g/L; MgSO$_4$, 0.024 g/L; sodium pyruvate, 0.3 g/L; pH 7.0) for 24–48 hours at 25° C. The culture was then centrifuged (8000 rpm, 15 min.) and resuspended into 10 ml sterile phosphate-buffered saline (NaCl, 9 g/L; KH$_2$PO$_4$, 6.85 g/L; pH 7.0–7.2). The culture was transferred to a 30 ml serum vial. MTBE was added to a concentration of 5 mg/L and stoppered and sealed. The degradation of MTBE was followed at 25° C. over several days. Table 3 shows an example of MTPE degraded by this pure culture from 5 mg/L to non-detectable concentrations (=5 µg/L) in 48 hours (Run #1). This culture was respiked with 5 mg/L MTBE. MTBE was degraded 95% (0.24 mg/L) in 27 hours (Run #2 Table 4).

TABLE 3

Run #1: Degradation of MTBE by Pure Culture

| Initial MTBE mg/L | MTBE after 48 hours |
|---|---|
| 5 | = 0.005 |

TABLE 4

Run #2: Degradation of MTBE by Pure Culture

| Initial MTBE mg/L | MTBE after 27 hours |
|---|---|
| 5 | 0.24 |

Part C: Physiological Properties of Pure Culture

Table 5 summarizes some physiological properties and substrates utilized by one of the MTBE-degrading isolates, SC-100. The organism is an aerobic, morphologically irregular, gram-positive rod. The organism appears coccal-shaped when cultured on solid media. It grows on Tweens, dextrin, cellobiose, fructose, lactose, maltose, trehalose, glucose, adonitol, arabinose, lactose, sorbitol and acetate. SC-100 also grows well on the metabolic intermediates in the MTBE pathway, namely, isopropanol, acetone and acetate. The culture grows well on a variety of complex bacteriological media including Trypticase Soy Broth and Agar (BBL, Becton Dickinson, Inc.) and Plate Count Agar (Difco). Based on physiological and biochemical features of SC-100 as a non-fermentative gram-positive, oxidase-negative, catalase-negative bacterium and substrate utilization patterns in the Oxi/Ferm and Biolog assays characteristics described in Bergey's Manual of Systematic Bacteriology, it is probable that this isolate belongs to the family of organisms known as actinomycetes. Further gene sequence and GC-FAME analyses confirmed that the pure culture belongs to the genus Rhodococcus.

TABLE 5

Physiological features & substrates utilized by pure culture isolate SC-100.

| FEATURE | REACTION |
|---|---|
| Morpthology | Large rod (about 1.0 micron diam.), non-motile |
| Gram stain | Positive |
| Pigment formed | Orange (intracellular) |
| Oxidase reaction | Negative[a)] |

TABLE 5-continued

Physiological features & substrates utilized
by pure culture isolate SC-100.

| FEATURE | REACTION |
|---|---|
| Optimum growth temp. | 20–35° C.; strict aerobe |
| Catalase | Negative |
| Feature Substrates utilized in Biolog assay[b] | Tween 40, Tween 80, betacyclodextrin, dextrin, cellobiose, fructose, lactulose, and trehalose |
| Substrates utilized in Oxi/Ferm Tube and Enterotube tests[c] | Glucose, adonitol, arabinose, lactose, sorbitol |
| Other substrates utilized[d] | Acetate, isopropanol, acetone, pentane, hexane, octane, decane, dodecane, tetradecane, hexadecane, maltose, mannitol, adipate, benzoate, citrate, lactate, tyrosine |
| Weak growth substrates[d] | MTBE, t-butyl alcohol, benzene, toluene, ethylbenzene, m-xylene |

[a]Oxidase reaction negative when grown on most substrates.
[b]Biolog Identification System, .GN and GP plates (Biolog, Inc; Hayward, CA) a carbon source utilization method for identification of gram-negative and gram-positive bacteria, Miller and Rhoden (J. Clin. Microbiol. 29(6) :143–147, 1991).
[c]Multimedia substrate utilization tubes for identification of oxidative and/or fermentative gam-negative rods (Hoffman-LaRoche, Inc.). Substrates tested in the Oxi/Ferm tube and Entertube include glucose, xylose, urea, citrate, arginine, lysine, lactose, sucrose, maltose, mannitol, dulcitol, phenylalanine and ornitine.
[d]Substrates were added to sterile minerals Bushnell Haas medium or the Rowbotham and Cross basal medium (J. Gen. Microbiol. 100:231–240, 1977) at concentrations of 100–200 mg C/L (or 0.1–1% w/v for sugars, acids and hydrocarbons) and growth evaluated (visual) after inoculating media with 1 ml of acetate-grown (24 hour) and incubating cultures for 7–14 days at 30 C.

Part D: 16S rRNA Gene Sequence Analysis

The 16S rRNA gene of the SC-100 pure culture was PCR amplified from genomic DNA isolated from SC-100 bacterial colonies. Primers used for the amplification correspond to *E. coli* positions 005 and 1540 (full length packages) and 005 and 531 (500 bp packages). Amplification products were purified from excess primers and dNTPs using Microcon 100 (Amicon) molecular weight cut-off membranes and checked for quality and quantity by running a portion of the products on an agarose gel.

Cycle sequencing of the 16S rRNA amplification products was carried out using AmpliTaq FS DNA polymerase and dRhodamine dye terminators. Excess dye-labeled terminators were removed from the sequencing reactions using Sephadex G-50 spin column. The products were collected by centrifugation, dried under vacuum and frozen at −20° C. until ready to load. Samples were resuspended in a solution of formamide/blue dextran/EDTA and denatured prior to loading. The samples were electrophoresed on a ABI Prism 377 DNA Sequencer. Data was analyzed using PE/Applied Biosystem's MicroSeq™ microbial analysis and DNA editing and assembly software and database.

The top ten alignment matches below are presented in a percent genetic distance format. In this format a low percent indicates a close match.

Alignment: 504 base pairs SC-100

4.56% 504 *Rhodococcus coprophilus*
4.57% 503 *Rodococcus rhodochrous*
5.80% 500 *Mycobacterium tokaiense*
6.40% 500 *Nocardia corynebacteroides*
6.41% 499 *Mycobacterium brumae*
6.97% 502 *Mycobacterium gadium*
7.20% 500 *Tsukamurella wratislaviensis*
7.37% 502 *Tsukamurella inchonensis*
7.37% 502 *Tsukamurella pulmonis*
7.37% 502 *Tsukamurella paurometabolum*

The Neighbor joining (Saitou and Nei, Mol. Biol. Evol. 4(4):406–425, 1987) phylogenetic trees below are generated using the above top ten alignment matches.

Neighbor Joining Tree

N Join: 3.294%

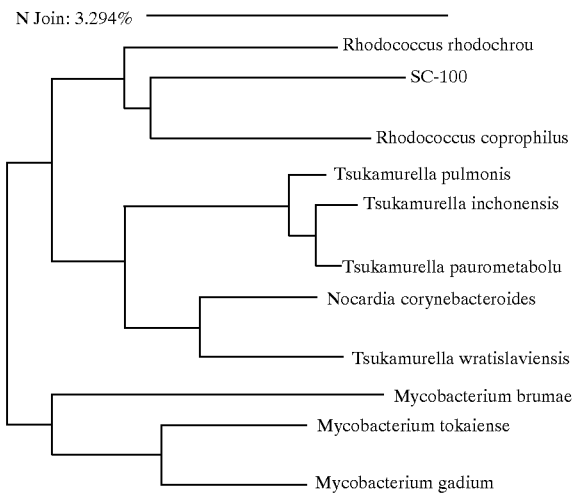

Concise alignments are also included below. These illustrate positions that differ between SC-100 and the is first match in the database. The position of the mismatch is read vertically from top to bottom and the sequences are read horizontally from left to right.

Concise Alignment - 500 bp

```
                        1111112222234444444444
                        6877799901256 7333456668
                        953891359136 13578960130
SC-100                  ATGTCTCGTCGCCCTCCGGGGAC
Rhodococcus coprophilus TCTATCTTATATTACGGATCCGT
```

Data from the partial sequencing of 16S rRNA have enabled the suprageneric relationship of actinomycetes to be established and this places Rhodococcus beside Nocardia and Mycobacterium among the nocardioform actinomycetes (Goodfellow, M 1989 Suprageneric classification of Actinomycetes, In: *Bergey's Manual of Systematic Bacteriology.* Pp. 2333–2339. Holt, J. G. Ed. Williams & Williams, Baltimore, Md.).

Part E: GC-Fame Analysis

The strain was streaked onto trypticase soy agar [TSA]. The TSA plates were prepared for use in the GC-FAME analyses after 24 hour incubation. The strain was examined against both the Aerobe (TSBA [rev. 3.90]) and the Clinical Aerobe (CLIN [rev. 3.90]) databases. The strain was subsequently prepared for Biolog analysis by suspending it in sterile saline and loading the solution into the appropriate microtiter plates (Gram positive). The plates were incubated for 24 hours and then examined against version 3.5 of the Biolog™ database using an automated microplate reader.

TABLE 6

Summary of Results by GC-FAME and Biolog ™

| Strain No. | Primary ID by GC-FAME | Sim. Coef | Dist. Coef | Primary ID by Biolog | Plate Type | Sim. Coef | Dist. Coef |
|---|---|---|---|---|---|---|---|
| SC-100 | *Rhodoccccus rhodochrous* [Clin] | 0.291 | 5.925 | No ID closest sp.: *Bacillus Brevis* | GP | 0.122 | 13.090 |

Part F: Degradation of MTBE with Pure Culture

Aqueous solutions containing various concentrations of MTBE: 5.7, 11.7, 20.9, 44.5, 90.2, 165, 350 ppm of MTBE were mixed with present pure culture SC-100 (2.76 g/L TSS at 25° C.) and incubated at 25° C. for various lengths of time and the centrations of MTBE were measured. The results of the experiment is listed in Table 7 below.

TABLE 7

| Time (hr) | MTBE Conc (ppm) | | | | | | |
|---|---|---|---|---|---|---|---|
| | 5.7 | 11.7 | 20.9 | 44.5 | 90.2 | 165 | 350 |
| 0 | 5.7 | 11.7 | 20.9 | 44.5 | 90.2 | 165 | 350 |
| 1 | 5.6 | 11.6 | 20.1 | 45 | 82.5 | 153 | 308 |
| 2 | 5.7 | 10.7 | 18.5 | 49 | 86 | 160 | 310 |
| 5 | 5.3 | 10.3 | 17.9 | 48.6 | 82.5 | 174 | 296 |
| 7 | 6.7 | 8.3 | 13.2 | 40.6 | 78.8 | 136 | 330 |
| 12 | 0.34 | 0.39 | 0.9 | 8.2 | 31.1 | 111 | 241 |
| 14 | 0 | 0 | 0 | 1.37 | 9.75 | 42 | 21.9 |
| 24 | | | 0 | 0 | 0 | 0 | 12.8 |

Part G: Degradation of MTBE with Pure Culture

Aqueous solutions containing various concentrations of MTBE: 6.5, 14, 19.2, 40, and 100 of MTBE were mixed with the present pure culture SC-100 (330 mg/L TSS at 9° C.) and incubated at 25° C. for various lengths of time and the concentrations of MTBE were measured. The results of the experiment is listed in Table 8 below.

TABLE 8

| Time (hr) | MTBE Conc (ppm) | | | | |
|---|---|---|---|---|---|
| | 6.5 | 14 | 19.2 | 40 | 100 |
| 0 | 6.5 | 14 | 19.2 | 40 | 100 |
| 0.5 | 5.5 | 10.8 | 19.2 | 37 | 100 |
| 1 | 4 | 9.4 | 15.4 | 30 | 90 |
| 4 | 2.1 | 5 | 14.1 | | 90 |
| 5 | 1.2 | 5.4 | 11.2 | 30 | 82 |
| 7 | 0.7 | 3.5 | 4.4 | 19 | 82 |
| 24 | 0 | 0.44 | 0.27 | 8.8 | 53.3 |
| 48 | | 0 | 0.08 | 0.11 | 26.4 |
| 72 | | | 0 | 0 | 23.9 |
| 96 | | | | | 10.8 |
| 168 | | | | | 0 |
| 192 | | | | | |

Part H: Degradation of TBA with Pure Culture

Aqueous solutions containing various concentrations of t-butyl alcohol (TBA) were mixed with the present pure culture SC-100 (820 mg/L TSS at 9° C.) and incubated at 25° C. for various lengths of time and the concentrations of TBA were measured. The results of the experiment is listed in Table 9 below.

TABLE 9

| Time (Day) | Run #1 TBA mg/L | Run #2 TBA mg/L | Run #3 TBA mg/L |
|---|---|---|---|
| 0.00 | 3.3 | 6.3 | 21 |
| 0.04 | 3.6 | 6.3 | 19 |
| 0.21 | 3.4 | 6.4 | 20 |
| 1 | 3.3 | 5.3 | 16 |
| 2 | 1.1 | 1.5 | 0.98 |
| 3 | 0.26 | 0.29 | 0.028 |
| 4 | 0.076 | 0.063 | 0.005 |

Part I: Effect of Storage Conditions (Temperature) on Rhodococcus Sp (Strain SC-100) Activity for MTBE Degradation A culture Medium ($BHC_{10}$) was prepared with BH+10 g/L Cerelose (1000 ml) at pH 7.2–7.4. $BHC_{10}$ was inoculated with 10–20 ml pure culture SC-100 grown on $BHC_1$ (BH+1 g/L Cerelose) for 2–4 days at room temperature. Assay MTBE Design in die-away test system was conducted using the following procedure:

a) 10 ml culture is added to a 30 ml serum vial, sealed, and 5–8 ppm of MTBE (0.5 ml of 200 ppm sterile soln) was subsequently introduced. Analysis was conducted on MTBE in vials using calibrated Photovac in aliquots of 0.1 ml sample.

b) Assay culture at 0 hr. in duplicates prior to set up at 25° C., 4° C. and −70 ° C.

c) Remove packed cell (pellet) aliquots at designated times; add 40 ml BH minerals solution; vortex well to suspend cells and remove 10 ml for die away test.

d) Determine Qmax mg MTBE/g TSS/hr.

The results of the study is summarized in Tables 10–13 below.

TABLE 10

MTBE DIE-AWAY (WASHED AND UNWASHED CULTURE)

| Culture Condition | MTBE ppm | | | | | | | |
|---|---|---|---|---|---|---|---|---|
| | 0 h | 3 h | 24 h | 48 h | 74 h | 99 h | 120 h | 186 h |
| Unwashed | 8.76 | 8.57 | 8.68 | 9.10 | 8.40 | 8.71 | 8.23 | 8.75 |
| Washed (2x)*(a) | 8.57 | 7.85 | .33 | 0 | | | | |
| Washed (2x)*(b) | 8.09 | 7.98 | .39 | 0 | | | | |

*Washed culture was centrifuged and resuspended in BH minerals 2x before running die-way assay.

TABLE 11

MTBE DIE-AWAY (WASHED CELLS)
24 HR STORED SAMPLES:

| Storage Culture Condition ° C. | MTBE ppm | | | |
|---|---|---|---|---|
| | 0 hours | 3 hours | 24 h | 50 h |
| 25 | 8.28 | 8.32 | 0 | |
| 4 | 7.96 | 7.79 | .47 | 0 |
| −70 | 7.97 | 8.36 | .55 | 0 |

TABLE 12

MTBE DIE-AWAY (WASHED CELLS)
48 HR STORED SAMPLES:
MTBE PPM

| Storage Culture Condition ° C. | 0 h | 3 h | 20 h |
|---|---|---|---|
| 25 C. | 9.12 | 7.54 | 0 |
| 4 | 8.83 | 7.26 | 0 |
| −70 | 8.61 | 7.27 | 0 |

TABLE 13

MTBE DIE-AWAY (WASHED CELLS)
72 HR STORED SAMPLES:
MTBE ppm

| Storage Culture Condition ° C. | 0 hr | 24 hr | 46 hr |
|---|---|---|---|
| 25 C. | 8.51 | .42 | 0 |
| 4 | 8.62 | 0 | |
| −70 | 8.57 | 0 | |

Therefore, the above data show that the pure culture did not show any significant deterioration in MTBE activities after 72 hours of storage.

Part J: Comparison of Degrading Activities in SC-100 and ATCC 15998

The degrading activities of the SC-100 Culture of the present invention, which belongs to Rhodococcus sp., was compared with the pure culture with ATCC No. 15998 which is a *Rhodococcus rhodochrous* "ruber strain"

TABLE 14

| CULTURE | MEDIUM/GROWTH CONDITIONS | INCUBATION/DAYS |
|---|---|---|
| 1. SC-100 | UGA + .01% Tyrosine | 30° C., 5d |
| 2. SC-100 | UGA + .1% Tyrosine | 30° C., 5d |
| 3. ATCC15998 | BHNPC10 (Cerelose 10 g/L) | 30° C., 4d |
| 4. ATCC15998 | UGAC10 (Cerelose 10 g/L) | 30° C., 6d |

One hundred mililiters of each of the cultures were centrifuged at 8000 rpm for 15 minutes and washed twice with sterile BH Mineral Solution. It was then resuspended to 10 ml BH and then sparged 20–30 seconds with 100% oxygen. Dispense 10 ml of the solution to 30 ml serium vials. The vials are sealed and about 10 ppm MTBE are added. MTBE die away test system was followed using the growth medium and conditions specified in Table 14 above. The results were analyzed with Photovac Gas Chromatography.

TABLE 15

MTBE CONDITIONS (DIE-AWAY) IN CULTURES
MTBE ppm

| Culture | 0 h | 3 h | 6 h | 25 h | 50 h |
|---|---|---|---|---|---|
| SC-100 (.01% Tyr) | 8.09 | 6.33 | 5.35 | 0.45 | 0 |
| SC-100 (.1% Tyr) | 8.39 | 8.60 | 2.26 | 0 | — |
| ATCC 15998 BHNPC$_{10}$ | 8.39 | 8.71 | 8.21 | 9.65 | 9.70 |
| ATCC 15998 UGAC$_{10}$ | 8.32 | 8.65 | 8.78 | 9.45 | 9.83 |

The results of the tests propose that the pure culture *Rhodococcus rhodochrous* "ruber strain" ATCC No. 15998 does not show the ability to degrading MTBE as demonstrated by the present pure culture.

Part K: Induction of MTBE Biodegradation in SC-100

The SC-100 culture was grown on a medium (100 ml) containing BH minerals (BH), 1 g/L $((NH_4)_2 SO_4)$, 1 g/L $K_2HPO_4$ and 10 g/L Cerelose (glucose) substrate. The culture was incubated on A shaker (200 rpm) at 30° C. for 48–72 hrs and then centrifuged at 8000 rpm for 15–20 minutes. The supernatant was decanted and the collected cells were washed twice in BH by the same centrifugation decanting procedure. After the final wash, the cell pellet is resuspended in 10 ml BH (w/o cerelose) and transferred first to a 30 ml serum bottle. The 20 ml headspace was fluidized with 100% $O_2$ and sealed with a butyl rubber stopper. MTBE was added in consecutive spikes at 10, 20, 40, 80 & 160 ppm and the biodegradation of MTBE by the culture was followed by taking a headspace sample (10–50 microliters) and determining the amount of MTBE using the Photovac GC (Model 10S Plus). In the induction method, doses of MTBE were added (from stock concentrated solutions of ether) in increasing concentrations after each previous dose was degraded e.g., after the 10 ppm dose degrades (e.g. 10–24 hr) then 20 ppm was added and the decline of MTBE in headspace was followed. This induction method is a method to induce the enzyme pathway in SC-100 that is responsible for biodegradation of the ether.

TABLE 16

MTBE Biodegradation in SC-100 Consecutive Spiking Experiment

| Time (Hours) | Concentration MTBE mg/L |
|---|---|
| 0 | 6.1 |
| 16 | 6.4 |
| 23 | 7.3 |
| 44 | 1.3 |
| 47 | 0.7 |
| 47 | 32.2 |
| 63 | 0 |
| 63 | 60.8 |
| 68 | 25.75 |
| 74 | 5.2 |
| 84 | 0 |
| 86.5 | 155 |
| 92.5 | 72.3 |
| 109.5 | 13.3 |
| 115.5 | 2 |
| 117.5 | 0.2 |
| 118 | 257 |
| 135.5 | 140 |
| 142 | 112 |
| 164 | 24.2 |
| 171.5 | 9.3 |
| 195.5 | 2.1 |

From the results of the above experiment, it can be seen that the MTBE degrading activity of the pure bacterial culture were induced to a higher level after the culture was exposed to MTBE for an extended period of time.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

What is claimed is:

1. A biologically pure bacterial culture having an ability to degrade at least 10% of the methyl-t-butyl ether (MTBE) present at a concentration of 0.01 to 500 ppm aerobically within 70 hours to carbon dioxide without adding propane, butane, isopropanol, acetone and ethanol; wherein said biologically pure bacterial culture is isolated from a mixed bacterial culture obtained by a process comprising the steps of:

adding an aqueous mixture comprising a first amount of activated sludge taken from a biotreater for treating wastewater in a Chemical Plant to a container, Adding a first portion of MTBE to said container to obtain a first mixture which contains from about 10 mg to about 500 mg of MTBE, incubating said first mixture at a temperature from about 10° C. to about 60° C., periodically adding additional amounts of the biosludge to said container, periodically withdrawing from the container from about 10% to about 70% of the supernatant medium followed by adding mineral solution to replace the supernatant withdrawn, and periodically adding MTBE to the container in an amount sufficient to maintain the concentration of MTBE in the mixture in the container at from about 10 mg to about 500 mg;

wherein said mixed bacterial culture also has an ability to degrade methyl-t-butyl ether (MTBE) aerobically to carbon dioxide within 70 hours, wherein said biologically pure bacterial culture is obtained by a process comprising the steps of:

(a) enhancing the isolation of said biologically pure bacterial culture from said mixed bacterial culture by a dilution enrichment process using MTBE and sterile nutrients-containing medium to obtain a dilute enrichment of said mixed culture, (b) transferring a portion of said dilute enrichment of said mixed culture from (a) to a sterile container comprising nutrients and solidifying agent, (c) incubating said container from (b) above to obtain colonies of bacteria, (d) transferring a portion of a colony from (c) above to a container and incubating it in presence of sterile nutrients and MTBE for a period of time, and (e) repeating step (d) until one of the colonies degrades MTBE to carbon dioxide after said incubating step of (d) above.

2. The biologically pure bacterial culture as described in claim 1, wherein said biologically pure bacterial culture also degrades t-butyl alcohol.

3. The biologically pure bacterial culture as described in claim 1, wherein said biologically pure bacterial culture belongs to the species Rhodococcus.

4. The biologically pure bacterial culture as described in claim 1, wherein the concentration of the MTBE degraded by the biologically pure bacterial culture in 10 hours is increased by at least 50% after being induced by said incubating.

5. A biologically pure bacterial culture having an ability to aerobically degrade at least 10% of methyl-t-butyl ether (MTBE) present at a concentration of 0.01 to 500 ppm to carbon dioxide within 70 hours without adding propane, butane, isopropanol, acetone and ethanol, wherein said biologically pure bacterial culture is isolated from a mixed bacterial culture isolated from an activated sludge taken from a biotreater for treating wastewater in a Chemical Plant, wherein said mixed bacterial culture also has an ability to degrade methyl-t-butyl ether (MTBE) aerobically to carbon dioxide within 70 hours, wherein said biologically pure bacterial culture is obtained by a process comprising the steps of:

(a) enhancing the isolation of said biologically pure bacterial culture from said mixed bacterial culture by a dilution enrichment process using MTBE and sterile nutrients-containing medium to obtain a dilute enrichment of said mixed culture, (b) transferring a portion of said dilute enrichment of said mixed culture from (a) to a sterile container comprising nutrients and solidifying agent, (c) incubating said container from (b) above to obtain colonies of bacteria, (d) transferring a portion of a colony from (c) above to a container and incubating it in presence of sterile nutrients and MTBE for a period of time, and (e) repeating step (d) until one of the colonies degrades MTBE to carbon dioxide after said incubating step of (d) above.

6. The biologically pure bacterial culture as described in claim 5, wherein said biologically pure bacterial culture belongs to the species Rhodococcus.

7. The biologically pure bacterial culture as described in claim 5, wherein said biologically pure bacterial culture degrades to carbon dioxide, MTBE and one or more of the following ether compounds: diisopropyl ether, ethyl-t-butyl ether, di-t-butyl ether, diisobutyl ether, isopropyl isobutyl ether, isopropyl t-butyl ether, t-amylmethyl ether, t-amylethyl ether, t-amyl ethyl ether, t-amyl propyl ether, t-amylisopropyl ether, t-amyl-n-butyl ether, t-amyl isobutyl ether, and t-amyl methyl ether within 70 hours.

8. The biologically pure bacterial culture of claim 5, wherein said biologically pure bacteria culture is capable of degrading to carbon dioxide, MTBE and one or more of the following tertiary carbon-containing ether compounds: ethyl-t-butyl ether, t-amyl-n-butyl ether, t-amylisobutyl ether, isopropyl t-butyl ether, t-amyl ethyl ether, t-amylpropyl ether, t-amylisopropyl ether, and methyl t-amyl ether within 70 hours.

9. A biologically pure bacterial culture of Rhodococcus species which has an ability to degrade aerobically at least 10% of methy-tert-butyl ether (MTBE) and t-butyl alcohol (TBA) present at a concentration of 0.01 to 500 ppm to carbon dioxide within 70 hours without adding propane, butane, isopropanol, acetone and ethanol.

10. The biologically pure bacterial culture as described in claim 9, wherein the MTBE degrading activity of said biologically pure bacterial culture is induced by incubating the biologically pure bacterial culture with MTBE.

11. The biologically pure bacterial culture as described in claim 10, wherein the concentration of the MTBE degraded by the biologically pure bacterial culture in 10 hours is increased by at least 50% after being induced by said incubating.

12. The biologically pure bacterial culture as described in claim 9, wherein said pure bacterial culture is gram positive.

13. The biologically pure bacterial culture as described in claim 9, wherein said pure bacterial culture is gram positive and the MTBE degrading activity of said biologically pure bacterial culture is induced by incubating the biologically pure bacterial culture with MTBE.

14. A composition made by adding a biologically pure bacterial culture which degrades aerobically at least 10% of methyl-t-butyl ether (MTBE) present at a concentration of 0.01 to 500 ppm to carbon dioxide within 70 hours without adding propane, butane, isopropanol, acetone and ethanol to a mixed bacterial culture which degrades MTBE within 70 hours.

15. The composition of claim 14, wherein said biologically pure bacterial culture is isolated from a mixed bacterial culture isolated from an activated sludge taken from a biotreater for treating wastewater in a Chemical Plant, wherein said mixed bacterial culture also has an ability to degrade methyl-t-butyl ether (MTBE) aerobically to carbon dioxide within 70 hours, wherein said biologically pure bacterial culture is obtained by a process comprising the steps of:
(a) enhancing the isolation of said biologically pure bacterial culture from said mixed bacterial culture by a dilution enrichment process using MTBE and sterile nutrients-containing medium to obtain a dilute enrichment of said mixed culture,
(b) transferring a portion of said dilute enrichment of said mixed culture from (a) to a sterile container comprising nutrients and solidifying agent,
(c) incubating said container from (b) above to obtain colonies of bacteria,
(d) transferring a portion of a colony from (c) above to a container and incubating it in presence of sterile nutrients and MTBE for a period of time, and
(e) repeating step (d) until one of the colonies degrades MTBE to carbon dioxide after said incubating step of (d) above.

16. A process for remediating groundwater, wastewater or soil containing methyl t-butyl ether (MTBE) to reduce the methyl t-butyl ether content thereof, which process comprises growing in the presence of said groundwater or wastewater under an aerobic condition a biologically pure bacterial culture; wherein said biologically pure bacterial culture degrades aerobically at least 10% of MTBE present at a concentration of 0.01 to 500 ppm to carbon dioxide within 70 hours without adding propane, butane, isopropanol, acetone and ethanol and is isolated from a mixed bacterial culture isolated from an activated sludge taken from a biotreater for treating wastewater in a Chemical Plant, wherein said mixed bacterial culture also has an ability to degrade at least 10% of methyl-t-butyl ether (MTBE) present at a concentration of 0.01 to 500 ppm aerobically to carbon dioxide within 70 hours, wherein said biologically pure bacterial culture is obtained by a process comprising the steps of:
(a) enhancing the isolation of said biologically pure bacterial culture from said mixed bacterial culture by a dilution enrichment process using MTBE and sterile nutrients-containing medium to obtain a dilute enrichment of said mixed culture,
(b) transferring a portion of said dilute enrichment of said mixed culture from (a) to a sterile container comprising nutrients and solidifying agent,
(c) incubating said container from (b) above to obtain colonies of bacteria,
(d) transferring a portion of a colony from (c), above to a container and incubating it in presence of sterile nutrients and MTBE for a period of time, and
(e) repeating step (d) until one of the colonies degrades MTBE to carbon dioxide after said incubating step of (d) above.

17. A process for degrading t-butyl alcohol (TBA) in a TBA-containing mixture, which process comprises growing in the presence of said TBA-containing mixture a biologically pure bacterial culture capable of degrading both TBA and methyl-t-butyl ether (MTBE); wherein said biologically pure bacterial culture degrades at least 10% of MTBE present at a concentration of 0.01 to 500 ppm aerobically to carbon dioxide within 70 hours without adding propane, butane, isopropanol, acetone and ethanol and is isolated from a mixed bacterial culture isolated from an activated sludge taken from a biotreater for treating wastewater in a Chemical Plant, wherein said mixed bacterial culture also has an ability to degrade methyl-t-butyl ether (MTBE) aerobically to carbon dioxide within 70 hours, wherein said biologically pure bacterial culture is obtained by a process comprising the steps of:
(a) enhancing the isolation of said biologically pure bacterial culture from said mixed bacterial culture by a dilution enrichment process using MTBE and sterile nutrients containing medium to obtain a dilute enrichment of said mixed culture,
(b) transferring a portion of said dilute enrichment of said mixed culture from (a) to a sterile container, comprising nutrients and solidifying agent,
(c) incubating said container from (b) above to obtain colonies of bacteria,
(d) transferring a portion of a colony from (c) above to a container and incubating it in presence of sterile nutrients and MTBE for a period of time, and
(e) repeating step (d) until one of the colonies degrades MTBE to carbon dioxide after said incubating step of (d) above.

18. A process for remediating groundwater, wastewater or soil containing both methyl t-butyl ether (MTBE) and TBA (t-butyl-alcohol) to reduce the methyl t-butyl ether and TBA content thereof, which process comprises growing in the presence of said groundwater, wastewater or soil under an aerobic condition a biologically pure bacterial culture, wherein said biologically pure bacterial culture degrades aerobically at least 10% of MTBE and TBA present at a concentration of 0.01 to 500 ppm to carbon dioxide within 70 hours without adding propane, butane, isopropanol, acetone and ethanol and is isolated from a mixed bacterial culture isolated from an activated sludge taken from a biotreater for treating wastewater in a Chemical Plant wherein said mixed bacterial culture also has an ability to degrade methyl-t-butyl ether (MTBE) and TBA aerobically to carbon dioxide within 70 hours, wherein said biologically pure bacterial culture is obtained by a process comprising the steps of:
(a) enhancing the isolation of said biologically pure bacterial culture from said mixed bacterial culture by a dilution enrichment process using MTBE and sterile nutrients-containing medium to obtain a dilute enrichment of said mixed culture,
(b) transferring a portion of said dilute enrichment of said mixed culture from (a) to a sterile container comprising nutrients and solidifying agent,
(c) incubating said container from (b) above to obtain colonies of bacteria,
(d) transferring a portion of a colony from (a) above to a container and incubating it in presence of sterile nutrients and MTBE for a period of time, and
(e) repeating step (d) until one of the colonies degrades MTBE to carbon dioxide after said incubating step of (d) above.

* * * * *